United States Patent [19]

Brown

[11] Patent Number: 4,768,613

[45] Date of Patent: Sep. 6, 1988

[54] DIRECTIONAL HEARING ENHANCEMENT

[76] Inventor: Shawn T. Brown, 125 N.W. Oregon Ave., Bend, Oreg. 97701

[21] Appl. No.: 1,405

[22] Filed: Jan. 8, 1987

[51] Int. Cl.$^4$ ............................................. H05R 25/00
[52] U.S. Cl. ..................................... 181/136; 181/129
[58] Field of Search ......................... 181/133, 136, 129

[56] References Cited

U.S. PATENT DOCUMENTS

| | | | |
|---|---|---|---|
| Re. 10,268 | 1/1883 | North | 181/133 |
| 269,078 | 12/1882 | MacDonald | 181/133 |
| 1,296,891 | 3/1919 | Williams | 181/136 |
| 1,761,666 | 6/1930 | Hinternesch | 181/133 |
| 2,012,877 | 8/1935 | Iwasa | 181/133 |
| 2,537,201 | 1/1951 | Amfitheatrof | 181/136 |
| 2,810,445 | 10/1957 | Garrido | 181/133 |

FOREIGN PATENT DOCUMENTS 286565 3/1928 United Kingdom ................ 181/136
832113 4/1960 United Kingdom ................ 181/136

*Primary Examiner*—B. R. Fuller
*Attorney, Agent, or Firm*—Chernoff, Vilhauer, McClung & Stenzel

[57] ABSTRACT

A device for improving the hearing acuity of a user directionally, including a pair of reflectors to be supported behind the user's ears so as to increase the effective area of the outer ear and reflect an increased amount of sound energy into the user's ears from a position in front of the user. The reflectors are supported alternatively on a headband or a cap equipped with horizontally extending straps which permit adjustment of the location of each reflector, and the reflectors are attached to the headband or straps by a respective base plate to which each reflector is attached pivotably so that the reflectors can be adjusted to optimum positions.

15 Claims, 1 Drawing Sheet

DIRECTIONAL HEARING ENHANCEMENT

BACKGROUND OF THE INVENTION

The present invention relates to improvement of human hearing ability, and in particular to a device for improving one's ability to perceive sounds originating from a particular direction, and to determine the direction from which such sounds are emanating, without the use of electronic amplifiers and the like.

The device of the present invention is particularly intended for use by hunters who would like to hear the sounds made by game birds or animals as they move, and to be able to determine the direction in which such game is located, even though human hearing acuity is normally somewhat less than that of most game animals and birds. The invention might also be used by spectators at sporting events, plays, and other public events, who would like better to hear what is said by the players, rather than what is said by persons seated behind them.

It has long been recognized that sound energy can be concentrated and guided to one's ears so as to be more easily audible. For example, ear trumpets were used long before electronic sound amplification was available for use in hearing aids. As taught in MacDonald U.S. Pat. No. 269,078 and in Hinternesch U.S. Pat. No. 1,761,666, a pair of ear trumpets of more or less complex construction can be interconnected with one another so as to include a structure extending over the top of one's head to hold the pair of ear trumpets with an end of each in place in a respective one of the user's ears. Such devices, while probably exhibiting some ability to aid in determining the direction from which sound emanates, are somewhat undesirable because of the necessity for extending into one's ear, and are unnecessarily complex in their construction, for one who has normal hearing capability.

What is desired, then, is a simple, inexpensive, non-electrical device for enhancing the ability of a person to hear and to determine the direction of origin of sounds, without the need to hold a device in the user's hands.

SUMMARY OF THE INVENTION

The present invention provides a simply constructed, yet adjustable device for effectively enhancing the size of one's outer ears so as to collect and direct toward the ears a greater amount of sound energy. This is accomplished according to the invention by providing a pair of reflectors, supported on a generally horizontal headband or an equivalent band attached to a hat, to suspend the reflectors behind one's ears, extending forward and diagonally away from the respective sides of the user's head so as to reflect sound energy into the user's ears. Preferably, the forward face of each reflector is concave, so as to focus the reflected sound on the user's ears. In a preferred embodiment of the invention each reflector is adjustable in position forwardly or rearwardly along the user's head, and is also pivotable so as to direct reflected sound optimally toward the user's ears.

It is therefore a principal object of the present invention to provide an improved device for enhancing one's ability to hear sounds of low intensity and to determine the direction of origin of such sounds, without the use of electronic microphones and amplifying devices.

It is another important object of the present invention to provide a device of the above-described nature in a form which makes the device useable by anyone, without having to provide different sizes of the device.

It is an important feature of the present invention that it includes a pair of portable sound reflectors, and a band for holding the reflectors in an optimum position with respect to the user's ears for reflecting sound energy into the ears.

It is another important feature of the present invention that it provides for support of sound reflectors movably, with each reflector being pivotable about a pair of non-parallel axes to provide reflection of sound in the direction which provides the optimum enhancement of one's ability to hear low intensity sounds.

It is yet a further feature of one embodiment of the invention that it includes supporting the sound reflectors by mounting them adjustably on a hat, so as to provide a more secure means of wearing such reflectors in a desired position with respect to the user's ears.

It is a principal advantage of the present invention that it enables one better to hear sounds coming from a frontal direction than from other directions and to do so better than has previously been possible without the use of devices of complex or expensive construction.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 2:
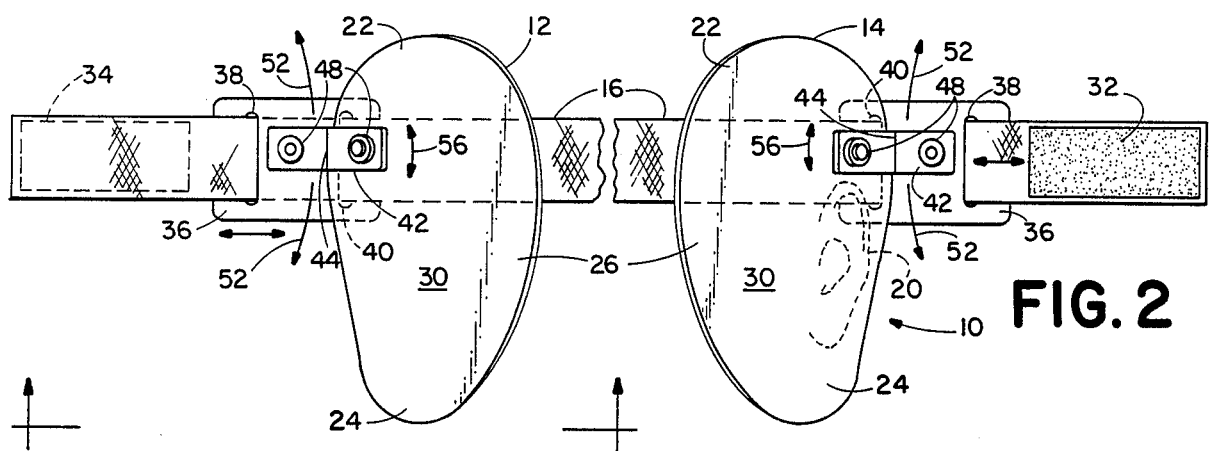
FIG. 2 is a view of the device shown in FIG. 1, spread out for clarity.
Figure 3:
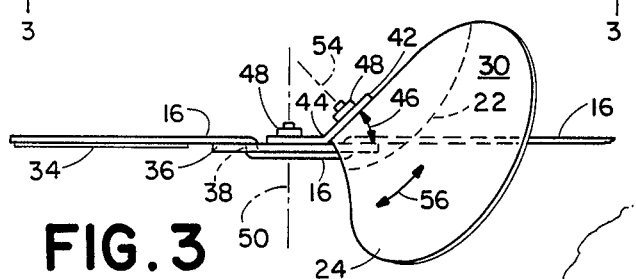
FIG. 3 is a bottom view of one of the sound reflectors and a portion of the headband and supporting connection of the device shown in FIG. 2, taken along line 3—3.
Figure 1:
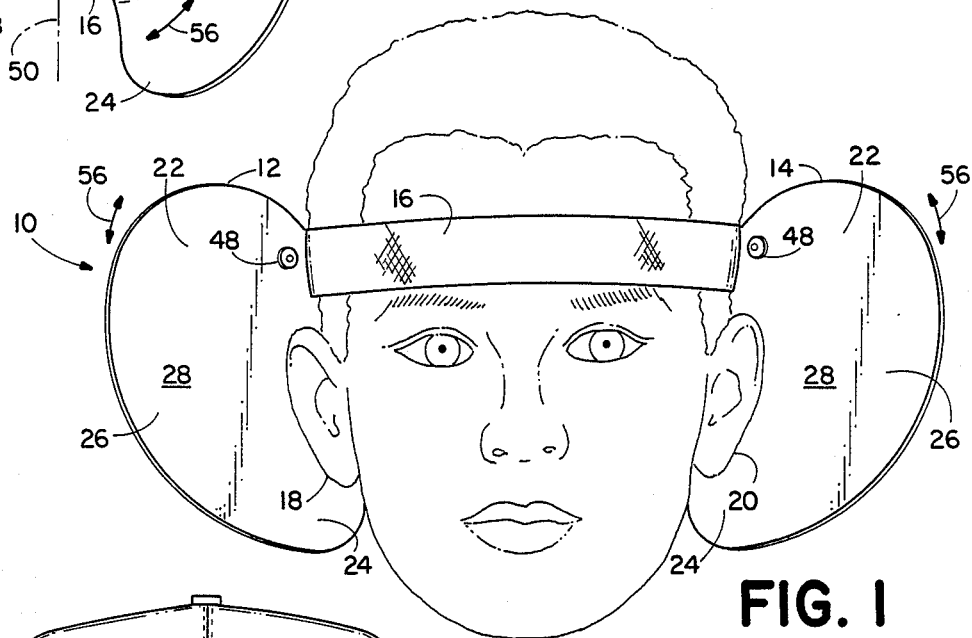
FIG. 1 is a front view of a person's head, with a device for enhancing directional hearing ability according to the present invention being worn.

Referring now to the drawings, in FIGS. 1-3, the present invention is embodied in a directional hearing aid device 10 including a pair of reflector members, a right reflector 12 and a left reflector 14, which are of similar but symmetrically opposite construction. The reflectors 12 and 14 are supported by a headband 16, horizontally encircling the head of a person using the device 10, as shown in FIG. 1, with the right reflector 12 located rearwardly adjacent the right ear 18, and the left reflector 14 located rearwardly adjacent the left ear 20. An upper portion 22 of each reflector extends upwardly above the top of the respective ear, and a lower portion 24 extends downwardly below the bottom of the respective ear. An outer portion 26 extends diagonally outward and forward beyond the respective ear, as may be seen best in FIG. 1, so that each of the reflectors 12 and 14 defines an acute angle with the respective nearest side of the wearer's head, the outer ear 18 or 20 thus being located within the acute angle defined between the wearer's head and the respective reflector 12 or 14. Each of the reflectors 12 and 14 is preferably formed of a sheet of material, for example an ABS plastic material which does not resonate acoustically to any significant degree, and which is thick enough and rigid enough to be self-supporting and hold a curved shape defining a concave front surface 28 and a convex back surface 30 of each reflector.

The headband 16 may be of a flexible woven webbing material having a width, for example, of about one and one-half inches (3.8 cm), and the opposite ends of the headband 16 are provided with elongate pieces of the mating opposite types of material forming a hook-and-loop fastening combination, such as the well-known material commonly known by the trade name Velcro. For example a patch 32 of hook-bearing material may be attached to the headband 16 near one end, while a patch 34 of loop pile material is attached proximate the opposite end of the head band on the opposite side of the webbing material, permitting the mating interconnection of the hooks and loops to hold the ends of the headband together to provide an adjustable circumference.

Each of the reflectors 12 and 14 is attached to the headband 16 by a base plate 36, which may be of similar plastic sheet material, and which is adjustable along the headband 16. The headband 16 extends through a pair of parallel vertical slots 38, 40 defined in each base plate 36, so that the base plate 36 is adjustable along the headband 16 to place the respective reflector in the desired position behind a user's ear, irrespective of the size of the user's head. When the head band 16 is in place on a user's head, tension in the headband 16 will ordinarily prevent the base plates 36 from slipping along the webbing material of the headband 16.

A support arm 42, also of similar plastic sheet material, is relatively elongate and somewhat narrower than the base plate 36. It extends generally horizontally and includes a bend 44 defining an obtuse angle between one end of the support art 42 and the other end of the support arm 42, which is fastened to and extends parallel with and along a portion of the base plate 36. The other end of the base plate 42 extends parallel with and is fastened to the respective reflector 12 or 14 to support it at the desired acute angle 46 between the front surface 28 and the base plate 36.

Preferably, each end of the support arm 42 is attached respectively to a base plate 36 or reflector 12 or 14 by a fastener such as a rivet 48. This permits the support arm 42 to be pivoted through an angle of at least a few degrees about an axis 50 extending substantially perpendicular to the base plate 36, as indicated by the arrows 52. Similarly, each of the reflectors 12 and 14 is pivotable about an axis 54, defined by one of the fasteners 48, extending substantially perpendicularly through the reflector 12 or 14 at the point of attachment to the support arm 42, as indicated by the arrows 56. As a result of the ability to pivot the support arms 42 and reflectors 12, 14 about the rivets 48 as indicated by the arrows 52 and 56, the lower portions 24 of the reflectors 12 and 14 may be adjusted in position to fit closely against the user's throat or jaw below the respective ear 18 or 20 so as to maximize the amount of sound reflected toward the user's ears. The rivets 48 or other fasteners are preferably tight enough to require some force to move the pivoted connections of the support arm, so that the reflectors 12, 14 will normally remain in their adjusted locations. The concavity of the front surface 28 helps to reflect the sound toward the ear, as will be appreciated.

Figure 4:
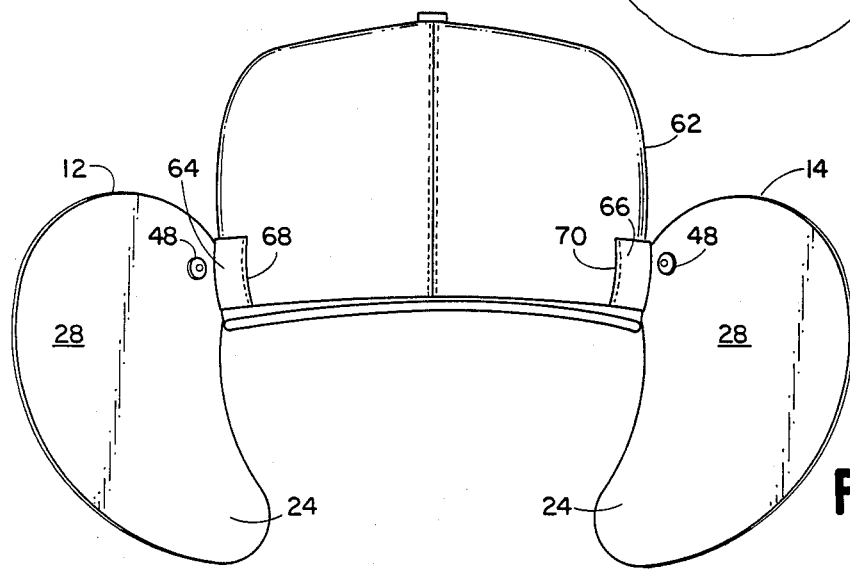
FIG. 4 is a front view of an embodiment of the invention incorporating a cap.

Referring to FIG. 4, in another embodiment of the invention, otherwise conventional headwear such as a cap 62 is provided with a pair of sidebands 64 and 66 located, respectively, on the right and left sides of the cap 62 and extending horizontally rearward from respective front ends 68 and 70 of the sidebands 64 and 66. The sidebands 64 and 66 may be of flexible webbing material similar to that of the headband 16, and end portions of each sideband are attached to the cap 62 as by stitching or the equivalent. The front ends 68 and 70 are located far enough forward with respect to the cap and the sidebands 64 and 66 extend generally horizontally rearward far enough to provide a desired amount of front-to-rear adjustability of the position of respective base plates 36. The construction of the right and left reflectors 12 and 14 is otherwise substantially similar to that shown in FIGS. 1–3 above.

For best results, the directional hearing aid device 10 is adjusted to place the right and left reflectors 12 and 14 behind the respective right and left ears 18 and 20 of the user and in close contact with the user's outer ears to extend their size effectively and reflect additional sound energy into the ears to be heard. The lower portions 24 of the right and left reflectors 12 and 14 will be placed as close as possible behind the ears 18 and 20, so as to maximize the effect of funneling sound into the ears 18 and 20. Sound originating in front of the user's head will naturally be heard best, and it will be possible to determine the direction from which sound is originating by turning one's head until a continuing or repeated sound is heard most clearly.

Preferably, when the directional hearing aid device 10 of the invention is to be used in hunting, it will be preferred to provide a surface finish which is not glossy, but dull and non-reflective of light, so that light will not be reflected from the reflector portions 12 and 14 as the user of the device 10 attempts to determine the direction from which sounds of an animal's voice or movement originate.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A device for improving hearing acuity directionally, comprising:
(a) support means for encircling the head of a person using the device, said support means including
   i. a length of flexible webbing material,
   ii. a base plate having a pair of spaced-apart slots,
   iii. an elongated support arm having a pair of ends, one of said ends being attached to said base plate and the other of said ends being attached to a respective one of said reflectors, and
   iv. said base plate being mounted on said webbing material with said webbing material extending through said pair of parallel slots; and
(b) a pair of reflectors of a size greater than the human outer ear, each reflector of said pair having a front surface and being supported adjustably by said support means, so as to be located rearwardly adjacent one of the person's ears, forming an acute angle between said front surface of the reflector and the side of the person's head, so as to reflect an increased amount of sound energy from positions in front of the person into the person's ears.

2. The device of claim 1, wherein said support means further comprises a cap having a band substantially encircling the head of the person using the device, wherein said webbing material is horizontally attached to said band of said cap.

3. The device of claim 1 wherein said length of flexible webbing material has a pair of opposite ends, the device further including a two-material hook-and-loop fastening system, a patch of a first material of said hook-and-loop fastening system being attached to a first of said opposite ends of said length of flexible webbing material and a mating patch of the other material of said hook-and-loop fastening system being attached to a second of said opposite ends of said length of flexible webbing material, and said length of flexible webbing material being arranged to encircle the head of the person using the device in a generally horizontal direction.

4. The device of claim 1 wherein said one of said ends of said support arm is attached pivotably to said base plate.

5. The device of claim 1 wherein said other of said ends of said support arm is attached pivotably to the respective one of the reflectors.

6. The device of claim 1 wherein said base plate is adjustably slidable along said strap of webbing material.

7. The device of claim 1 wherein said one of said ends of said support arm is pivotable about an axis extending perpendicular to the base plate.

8. The device of claim 1 wherein said other of said ends of said support arm is pivotable about an axis perpendicular to the respective one of the reflectors.

9. The device of claim 1 wherein the front surface of each of said reflectors is concave.

10. The device of claim 1 wherein each of said reflectors is of a non-reverberating plastics material.

11. The device of claim 10 wherein each of said reflectors is of ABS sheet plastic material.

12. The device of claim 1 wherein said front surface of each of said reflectors has a low reflectivity of light.

13. The device of claim 1 wherein each of said reflectors has the general shape of the outline of the human outer ear.

14. The device of claim 1 wherein each reflector is forwardly concave, each reflector having upper and lower portions which extend arcuately forward.

15. A device for improving hearing acuity directionally, comprising:
(a) support means for encircling the head of a person using the device, said support means including a cap having sides and respective sidebands of flexible webbing material fixedly attached thereto, a portion of said webbing material extending generally horizontally along a portion of said cap on each of said sides thereof; and
(b) a pair of reflectors of a size greater than the human outer ear, means for mounting said reflectors slidably on said portion of said webbing material so that each of said reflectors can be positioned, so as to be located rearwardly adjacent one of the person's ears, forming an acute angle between said front surface of the reflector and the side of the person's head, so as to reflect an increased amount of sound energy from positions in front of the person into the person's ears.

* * * * *